US00PP19093P2

(12) United States Plant Patent
Verduin

(10) Patent No.: US PP19,093 P2
(45) Date of Patent: Aug. 12, 2008

(54) ***ASTILBE* PLANT NAMED 'LOVE AND PRIDE'**

(50) Latin Name: *Astilbe chinensis*
Varietal Denomination: Love and Pride

(75) Inventor: Henricus Gijsbertus Johannes Verduin, Heemskerk (NL)

(73) Assignee: Witteman & Co., Hillegom (NL)

( * ) Notice: Subject to any disclaimer, the term of this patent is extended or adjusted under 35 U.S.C. 154(b) by 0 days.

(21) Appl. No.: 11/728,163

(22) Filed: Mar. 23, 2007

(51) Int. Cl.
*A01H 5/00* (2006.01)

(52) U.S. Cl. ..... Plt./407; Plt./263

(58) Field of Classification Search ..... Plt./407, Plt./263

See application file for complete search history.

*Primary Examiner*—Kent L. Bell
*Assistant Examiner*—S. B. McCormick-Ewoldt
(74) *Attorney, Agent, or Firm*—C. A. Whealy

(57) ABSTRACT

A new and distinct cultivar of *Astilbe* plant named 'Love and Pride', characterized by its upright and sturdy plant habit; strong and healthy foliage; freely and uniformly flowering habit; red purple-colored flowers; and good garden performance.

3 Drawing Sheets

Botanical designation: *Astilbe chinensis.*
Cultivar denomination: 'Love and Pride'.

BACKGROUND OF THE INVENTION

The present invention relates to a new and distinct cultivar of *Astilbe,* botanically known as *Astilbe chinensis* and hereinafter referred to by the name 'Love and Pride'.

The new *Astilbe* is a product of a planned breeding program conducted by the Inventor in Heemskerk, The Netherlands. The objective of the breeding program was to create new *Astilbe* cultivars with healthy foliage and attractive flower coloration.

The new *Astilbe* originated from a cross-pollination made by the Inventor in 1998 in Heemskerk, The Netherlands, of two unidentified selections of *Astilbe chinensis,* not patented. The new *Astilbe* was discovered and selected by the Inventor as a single flowering plant within the progeny of the stated cross-pollination in a controlled environment in Heemskerk, The Netherlands in July, 1999.

Asexual reproduction of the new *Astilbe* by divisions in a controlled environment in Heemskerk, The Netherlands since January, 2000, has shown that the unique features of this new *Astilbe* are stable and reproduced true to type in successive generations.

SUMMARY OF THE INVENTION

The cultivar Love and Pride has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Love and Pride'. These characteristics in combination distinguish 'Love and Pride' as a new and distinct cultivar of *Astilbe:*

1. Upright and sturdy plant habit.
2. Strong and healthy foliage.

3. Freely and uniformly flowering habit.
4. Red purple-colored flowers.
5. Good garden performance.

Plants of the new *Astilbe* and the parent selections differ primarily in flower coloration and plant height.

Plants of the new *Astilbe* can be compared to plants of the cultivar Finale, not patented. In side-by-side comparisons conducted in Heemskerk, The Netherlands, plants of the new *Astilbe* and the cultivar Finale differed in the following characteristics:

1. Plants of the new *Astilbe* were slightly taller than plants of the cultivar Finale.
2. Plants of the new *Astilbe* were sturdier than plants of the cultivar Finale.
3. Plants of the new *Astilbe* flowered earlier than plants of the cultivar Finale.
4. Plants of the new *Astilbe* had brighter red purple-colored flowers than plants of the cultivar Finale.

Plants of the new *Astilbe* can also be compared to plants of the cultivar Cattleya, not patented. In side-by-side comparisons conducted in Heemskerk, The Netherlands, plants of the new *Astilbe* and the cultivar Cattleya differed in the following characteristics:

1. Plants of the new *Astilbe* were slightly taller than plants of the cultivar Cattleya.
2. Leaves of plants of the new *Astilbe* were pubescent whereas leaves of plants of the cultivar Cattleya were glabrous.
3. Plants of the new *Astilbe* flowered later than plants of the cultivar Cattleya.

BRIEF DESCRIPTION OF THE PHOTOGRAPHS

The accompanying colored photographs illustrate the overall appearance of the new *Astilbe,* showing the colors as true as it is reasonably possible to obtain in colored reproductions of this type. Colors in the photographs may differ slightly from the color values cited in the detailed botanical description which accurately describe the colors of the new *Astilbe.*

The photograph on the first sheet comprises a side perspective view of a typical flowering plant of 'Love and Pride' grown in a container.

The photograph at the top of the second sheet is a close-up view of a typical inflorescence of 'Love and Pride'.

The photograph at the bottom of the second sheet is a close-up view of typical flowers of 'Love and Pride'.

The photograph on the third sheet is a close-up view of the upper surface of a typical leaf of 'Love and Pride'.

DETAILED BOTANICAL DESCRIPTION

The aforementioned photographs and following observations, measurements and values describe plants grown in containers in Heemskerk, The Netherlands, under commercial practice during the early autumn in an outdoor nursery with day temperatures ranging from 12° C. to 32° C. and night temperatures ranging from 12° C. to 16° C. Plants had been growing for about one year when the photographs and description were taken. In the following description, color references are made to The Royal Horticultural Society Colour Chart, 2001 Edition, except where general terms of ordinary dictionary significance are used.

Botanical classification: *Astilbe chinensis* cultivar Love and Pride.

Parentage:

*Female, or seed, parent.*—Unidentified selection of *Astilbe chinensis,* not patented.

*Male, or pollen, parent.*—Unidentified selection of *Astilbe chinensis,* not patented.

Propagation:

*Type.*—By divisions.

*Time to initiate roots.*—About 20 days at 15° C.

*Time to produce a rooted plant.*—About 50 days at 20° C.

*Root description.*—Fine; white in color.

*Rooting habit.*—Freely branching.

Plant description:

*Plant form/habit.*—Herbaceous perennial. Upright and sturdy plant habit; roughly triangular. Flowering stems and leaves basal; dense and bushy growth habit; moderately vigorous to vigorous growth habit. Freely and uniformly flowering with numerous flowers on branched panicles.

*Growth rate.*—Moderate to fast; from divisions, about 18 weeks are required to produce fully-grown flowering plants.

*Plant height* (*soil level to top of foliar plant*).—About 58.5 cm.

*Plant height* (*soil level to top of inflorescences*).—About 93 cm.

*Plant width* (*spread*).—About 90.8 cm.

*Stem description.*—Length: About 54.8 cm. Diameter: About 4 mm. Internode length: About 16.7 cm. Strength: Strong. Texture: Sparsely pubescent. Color: 144A.

Foliage description:

*Arrangement.*—Alternate; biternately compound.

*Leaf length* (*excluding petiole*).—About 33.6 cm.

*Leaf width.*—About 29.7 cm.

*Lateral leaflet length.*—About 5.1 cm.

*Lateral leaflet width.*—About 2.8 cm.

*Terminal leaflet length.*—About 7.5 cm.

*Terminal leaflet width.*—About 4.1 cm.

*Lateral and terminal leaflet shape.*—Ovate to narrowly ovate.

*Lateral and terminal leaflet apex.*—Acute.

*Lateral and terminal leaflet base.*—Attenuate.

*Lateral and terminal leaflet margin.*—Biserrate.

*Lateral and terminal leaflet texture, upper and lower surfaces.*—Sparsely pubescent; slightly rough.

*Lateral and terminal leaflet venation pattern.*—Pinnate.

*Lateral and terminal leaflet color.*—Developing leaves, upper surface: 143A. Developing leaves, lower surface: Between 138A and 143A. Fully expanded leaves, upper surface: 137B; venation, 145A. Fully expanded leaves, lower surface: 137C; venation, 144C.

*Leaf petiole length.*—About 17.9 cm.

*Leaf petiole diameter.*—About 3 mm.

*Leaflet petiole length.*—About 4.8 cm.

*Leaflet petiole width.*—About 3 mm.

*Leaf and leaflet petiole texture, upper and lower surfaces.*—Smooth, glabrous.

*Leaf and leaflet petiole color, upper and lower surfaces.*—144B; at the nodes, 175A to 175B.

Flower description:

*Flower type/habit.*—Numerous single rotate flowers arranged on branched panicles; flowers fact upright, outward or downward depending on position on the panicle. Panicles conical in shape. Freely and uniformly flowering habit with about 1,000 flower buds and flowers developing per inflorescence; typically twelve panicles develop per plant.

*Fragrance.*—Faintly fragrant; sweet.

*Natural flowering season.*—Continuously flowering during the summer and late summer in Heemskerk, The Netherlands.

*Postproduction longevity.*—Flowers last about ten days on the plants. Flowers persistent.

*Flower buds.*—Height: About 2.5 mm. Diameter: About 2 mm. Shape: Broadly ovoid. Color: 60B to 60C; towards the base, 145C.

*Inflorescence height.*—About 25.9 cm.

*Inflorescence diameter.*—About 13.5 cm.

*Flower diameter.*—About 1 cm.

*Flower depth.*—About 7 mm.

*Petals.*—Quantity per flower: Typically five in a single whorl. Length: About 7 mm. Lobe width: About 1 mm. Shape: Narrowly oblanceolate. Apex: Acute. Margin: Entire. Texture, upper and lower surfaces: Smooth, glabrous. Color: Developing petals, upper and lower surfaces: 76A to 76C. Fully expanded petals, upper and lower surfaces: 76A to 76C; color becoming closer to 77C with development.

*Sepals.*—Quantity per flower: Typically five in a single whorl, fused towards the base; campanulate calyx. Length: About 2 mm. Width: About 1.2 mm. Shape: Ovate. Apex: Acute. Margin: Entire. Texture, upper and lower surfaces: Smooth, glabrous. Color, developing sepals, upper and lower surfaces: 60B to 60C; towards the base, 145C. Color, fully expanded sepals, upper and lower surfaces: 145C; towards the apex, 60C.

*Peduncles.*—Length: About 25.3 cm. Diameter: About 2.5 mm. Angle: Erect. Strength: Strong. Texture: Smooth, glabrous. Color: 182A.

*Pedicels.*—Length: About 1 mm. Diameter: About 0.5 mm. Angle: About 45° from vertical. Strength: Moderately strong. Texture: Smooth, glabrous. Color: Between 182D to 145B.

*Reproductive organs.*—Stamens: Quantity per flower: Typically ten; anthers basifixed. Filament length: About 3.5 mm. Anther shape: Oblong. Anther length: About 0.2 mm. Anther color: 156D. Pollen amount: Scarce. Pollen color: 155D. Pistils: Quantity per flower: Two. Pistil length: About 2.5 mm. Stigma shape: Club-shaped. Stigma color: 60D. Style length: About 2.3 mm. Style color: N155B to N155C. Ovary color: 65C to 65D.

*Seed/fruit.*—Seed and fruit development have not been observed.

Disease/pest resistance: Plants of the new *Astilbe* have not been noted to be resistant to pathogens and pests common to *Astilbe*.

Garden performance: Plants of the new *Astilbe* have been observed to have good garden performance and tolerate rain, wind and high temperatures of about 35° C. Plants of the new *Astilbe* have been observed to be hardy to USDA Zone 5.

It is claimed:

1. A new and distinct *Astilbe* plant named 'Love and Pride' as illustrated and described.

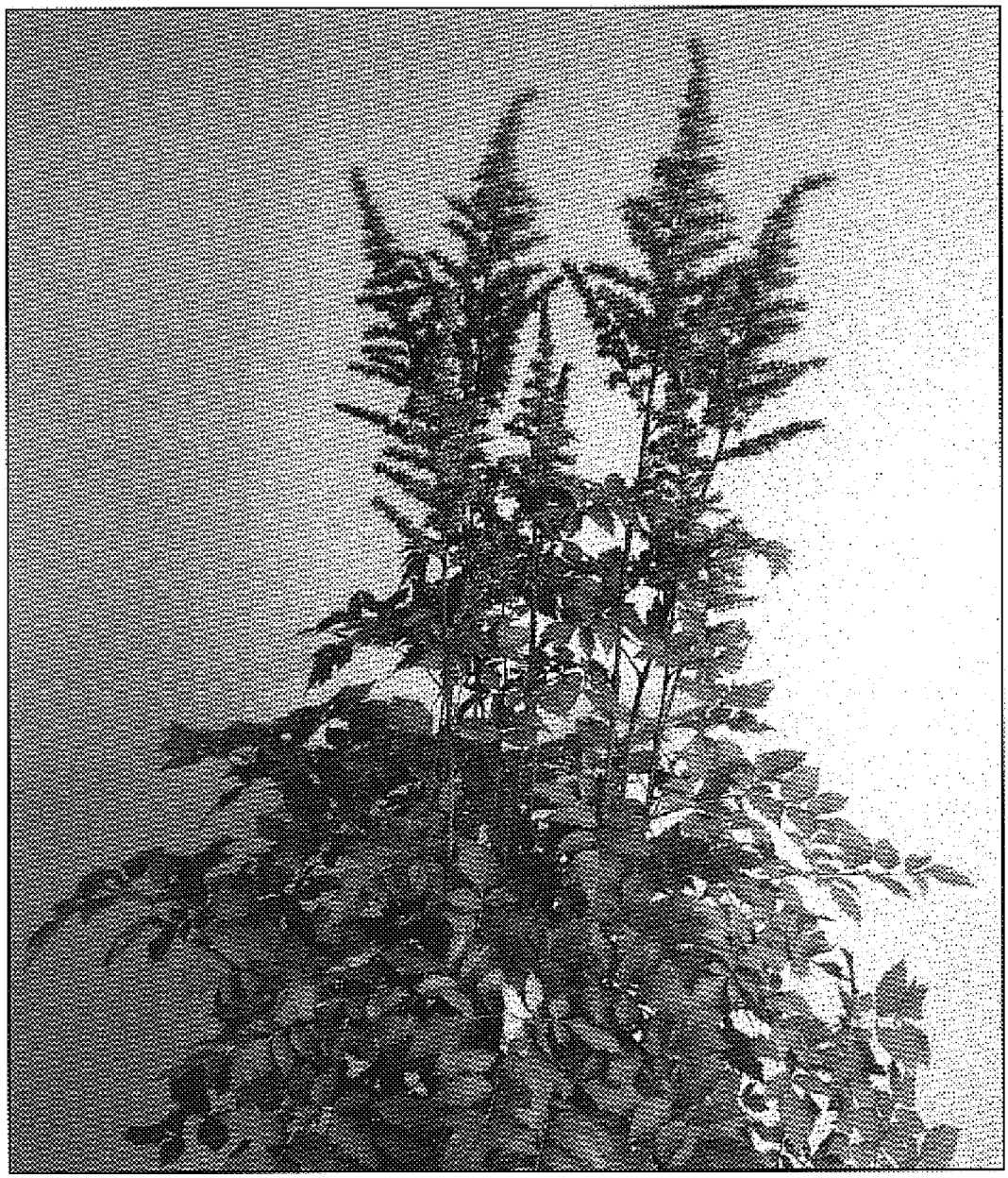

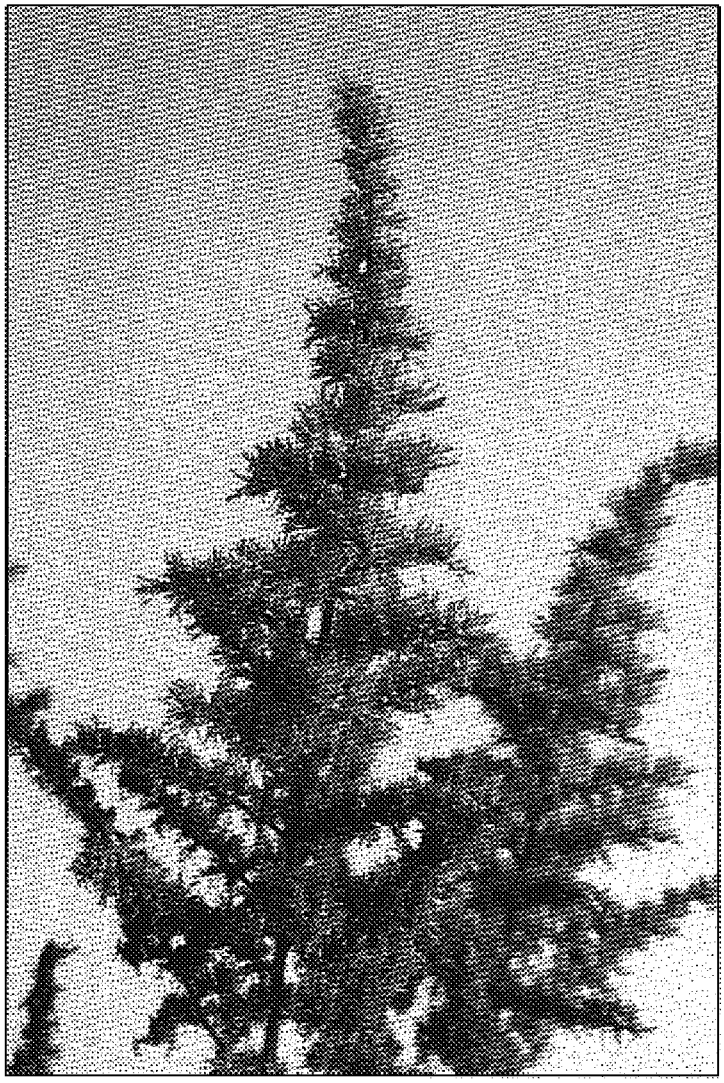
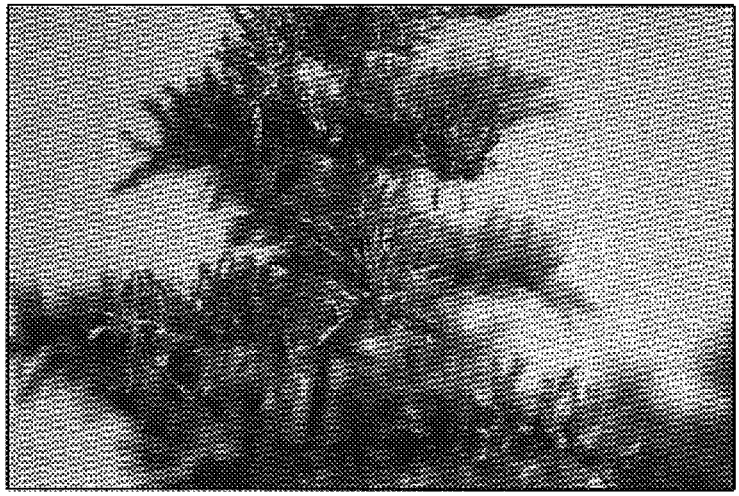

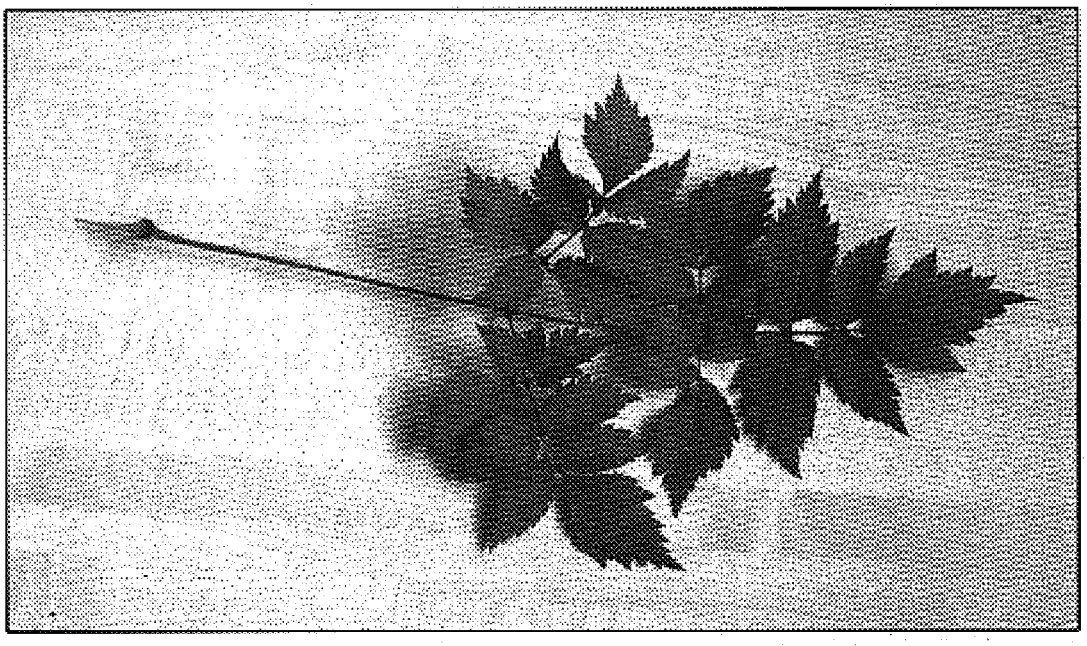

* * * * *